United States Patent
Lan et al.

(10) Patent No.: US 7,150,972 B2
(45) Date of Patent: Dec. 19, 2006

(54) **STEROL CARRIER PROTEIN-2 FROM THE MOSQUITO, *AEDES AEGYPTI***

(75) Inventors: Que Lan, Madison, WI (US); Kendall C. Krebs, Waterloo, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/823,203

(22) Filed: Apr. 13, 2004

(65) Prior Publication Data

US 2004/0211865 A1    Oct. 28, 2004

Related U.S. Application Data

(60) Provisional application No. 60/465,648, filed on Apr. 25, 2003.

(51) Int. Cl.
*G01N 33/53* (2006.01)

(52) U.S. Cl. ............... 435/7.1; 435/6; 435/7.9; 435/7.1; 435/7.93; 435/325; 530/350; 530/300; 514/12

(58) Field of Classification Search ................. 435/7.1, 435/325, 6, 7.9, 7.93; 530/350, 300; 514/12
See application file for complete search history.

(56) References Cited

OTHER PUBLICATIONS

Seffernick et al. (J. Bacteriology, vol. 183, pp. 2405-2410, 2001).*
Krebs et al. (Insect Molecular Biology, vol. 12, No. 1, pp. 51-60, 2003).*
Wells, (Biochemistry, vol. 29, pp. 8509-8517, (1990).*
Murphy et al., (Journal of Lipid Research, vol. 41, pp. 788-796, 2000).*
Atshaves et al., (Journal of Lipid Research, vol. 44, pp. 1751-1762, (2003).*
Baum, C.L. et al. 1993. J Lipid Res 34(5):729-39.
Baum, C.L. et al. 1997. J Biol Chem 272(10):6490-6498.
Borovsky, D. et al. 1986. Arch Insect Biochem Physiol 3(1):19-30.
Bun-Ya, M. et al. 2000. Cell Biochem Biophys 32 Spring:107-16.
Colles, S.M. et al. 1995. Lipids. 30(9):795-803.
Dwivedy, A.K. et al. 1982. Entomon 7(4):411-422.
Dyer, D.H. et al. 2003. J Biol Chem 278:39085-39091.
Feldlaufer, M.F. et al., 1995. Insect Biochem Mol Biol 25(6):709-12.
Frolova, A. et al. 1996. J Biol Chem 271(50):31878-84.
Fuchs, M. et al. 2001. J Biol Chem 276(51):48058-65.
Gallegos, A.M. et al. 2000. Chem Phys Lipids 105(1):9-29.
Gallegos, A.M. et al. 2001. Prog Lipid Res 40(6):498-563.
Hagedorn, H. H. et al. 1975. Proc Natl Acad Sci U S A 72(8):3255-9.
Ohba, T. et al. 1995. Biohemistry 34(33):10660-8.
Ossendorp, B.C. et al. 1990. Biochem Biophys Res Commum 168(2):631-6.
Pfeifer, S.M. et al. 1993a. Arch Biochem Biophys 304(1):287-93.
Pfeifer, S.M. et al. 1993b. Mol Biol 47(1-6)167-172.
Puglielli, L. et al. 1995. J Biol Chem 270(32):18723-6.
Schroeder, F. et al 2000. J Biol Chem 275(33):25547-55.
Seedorf, U. et al 1991. J Biol Chem 266(1):630-6.
Seedorf, U. et al. 1998. Genes Dev 12(8):1189-201.
Seedorf, U. et al. 2000. Biochim Biophys Acta 1486(1):45-54.
Stolowich, N.J. et al. 2002. Cell Mol Life Sci 59(2):193-212.
Sviridov, D. 1999. Histol Histopathol 14(1):305-19.
Svoboda, J.A. et al. 1995. Lipids 30(3):263-267.
Tan, H. et al. 1990. Eur J Biochem 190(1):107-12.
Van Heusden, G.P. et al. 1990. Biochim Biophys Acta 1046(3):315-21.
Xu, T. et al. 1991. J Biol Chem 266(11):6801-6807.

* cited by examiner

*Primary Examiner*—Hope Robinson
(74) *Attorney, Agent, or Firm*—Godfrey & Kahn, S.C.

(57) ABSTRACT

The invention provides AeSCP-2 polypeptides, polynucleotides encoding AeSCP-2 polypeptides, and methods for producing such materials by recombinant techniques. Also provided are methods for utilizing AeSCP-2 polypeptides to screen for compounds exhibiting antagonist or agonist activity toward AeSCP-2 biological activity, in particular, cholesterol transport.

2 Claims, 6 Drawing Sheets

5'gatcagtttcgagttgtccacttgaagttctgttgaaaaaccaaaccaccctccaaa<u>ATG</u>TCTCTGAAGTCCGACGA
                                                            M  S  L  K  S  D  E AGTTTTCGCCAAGATCGCTAAGCGTCTGGAGAGCATCGACCCCGCCAACCGTCAGGTCGAGCACGTGTACAAGTTCAGA
 V  F  A  K  I  A  K  R  L  E  S  I  D  P  A  N  R  Q  V  E  H  V  Y  K  F  R ATCACCCAGGGTGGCAAGGTTGTCAAGAACTGGGTTATGGATCTGAAGAACGTCAAGCTGGTCGAGTCCGACGATGCCG
 I  T  Q  G  G  K  V  V  K  N  W  V  M  D  L  K  N  V  K  L  V  E  S  D  D  A  A CCGAGGCCACCCTGACCATGGAGGATGACATCATGTTCGCCATCGGAACCGGTGCCCTGCCCGCCAAGGAAGCCATGGC
 E  A  T  L  T  M  E  D  D  I  M  F  A  I  G  T  G  A  L  P  A  K  E  A  M  A CCAGGACAAGATGGAAGTCGATGGACAAGTTGAGCTGATCTTCCTGCTGGAGCCATTCATTGCCTCGCTGAAG<u>TAA</u>aat
 Q  D  K  M  E  V  D  G  Q  V  E  L  I  F  L  L  E  P  F  I  A  S  L  K  (SEQ ID NO:3)

gcg<u>tga</u>cgcggcccttgtgaataccaatcattgcatgtgcttgcctcgtttaatcagagcgaatgtcatgtcatccaaa ctactgtgttgtaacttattatttttcctgtatcgcgatttcggcatcattaaaacgtattttgtaaagtaaaaaaaaa aaaaaaaaaaaaaaaaaaaaa3'   (SEQ ID NO:2)

FIG. 1

```
                                                  +                        ***********
Aedes        1  --------------------MSLKSDEVFAKIAKRLESI---DPANRQVEHVYKFRITQG-GKVVKNWVMDLKNVKLVES
Anopheles    1  ------------YCPSAQRVRQLL·A····P··ER············-···N····QQ·····Q·N-·T···T··L···A···T·G
rat          1                     SSAGDGF·ANLI·KE·E·K··EEG--EEFVKKIGGIFA·KV·D·P···EAT··V·V··G·GSVL
human        1                     SSASDGF·ANL··KE·E·K··EEG--EQFVKKIGGIFA·KV·D·P····AT··V·V··G·GSVL
DmSCP-X     420 -------------------DGF·VAPLLKLLEQAMQEDK--NLIEK·RAI·G·KVN··PN·QTGF··I·A·QG·GKII
CG11151      1  -------------------···Q··A··Q··IDG·KEN---EAKAKA·NG·FLYK··KD-···A·E·TL·C··A·AY·G
CG12269      1  -------------------M·····IIE··RNK·KES----···R·T·VNTFQ·NFTDAD·NLI·MA··IYEGSATS-
nematodes   316                   ----------------------VAS·AMD---EHLV·LIGR·FQINCKD----IEP-ICI···HGSGSAY
yeast        1  -------------------MSVEVDGFNASPL·KELNEG-ADKAKAQE·VKA·NAIIVITLKNK-EGKEQS··L···KAGTLAK +                     **    *  *  **
consensus       ---------------------······PL·QELEEAVKELG--EELVKK·GAILE·NVKD·-TGKEDA·TI····G·G·VY

***   *+********                +++++
Aedes        57 -DDA---AEATLTMEDDIMFAIGTGALPAKEAMAQDKMEVDGQVELIFLLEPFIASLK--------   (SEQ ID NO:3)
Anopheles    70 -·GP---··················M····L····LD·E···············K--------   (SEQ ID NO:4)
rat          63 P·SDK-K·DC·I··A·SDLL·LM··KMNPQS·FF·G·LKIA·NMG·AMK·QSLQLQPDK-----AKL   (SEQ ID NO:5)
human        63 PNSDK-K·DC·I··A·SDFL·LM··KMNPQS·FF·G·LKIT·NMG·AMK·QNLQLQPGN-----AKL   (SEQ ID NO:6)
DmSCP-X     479 FNGTQ-KCDV·FIIS··DV·ELL··K··PQK·FF·G·IKIQ·NMGFAMK·MDLQDPPKAGSRLRSKL   (SEQ ID NO:7)
CG11151      58 -PAQGIKVDT···VA·ED·VD·AL·K·NPQA·FMKG·LKIA·NIM·TQK·A·LLKTD-------AKL   (SEQ ID NO:8)
CG12269      55 -------VD·QV·IS·EDFYLV··KQKTFQ·VLQ·E·AKI··DE·A·NKMLEKFRINSQN-------   (SEQ ID NO:9)
nematodes   357 -KGTSLNPDVVFETSLEVFGK·L··KEVSPVTVY·NGNLVKK·SIQDAMQ·KHLVERMSD------WL   (SEQ ID NO:10)
yeast        65 V·G·VPKGDVQ·ILK·VDFVKLANNKVNGQ·LFMNG·LKVK·NMMKATAI·SVFKKLDP----RPKL   (SEQ ID NO:11)

***·***  +*  ****  *           +++  +
consensus       GGG·ANK·DV·FSAS·SDFLK·L··K·DPQT·FM·G·LKIK·NMM·AMK·MAVLKKFL---------
```

FIG. 2

STEROL CARRIER PROTEIN-2 FROM THE MOSQUITO, *AEDES AEGYPTI*

CROSS-REFERENCE TO RELATED APPLICATIONS

This application claims the benefit of U.S. Provisional application 60/465,648, filed Apr. 25, 2003, incorporated herein by reference.

STATEMENT AS TO RIGHTS TO INVENTIONS MADE UNDER FEDERALLY SPONSORED RESEARCH OR DEVELOPMENT

This work was supported in part by an award from the United States government-USDA-CSREES 02-CRHF-02-6055. The Government of the United States may have certain rights in this invention.

FIELD OF THE INVENTION

This invention relates generally to cholesterol transport. In particular, this invention is directed to nucleic acids encoding *Aedes aegypti* sterol carrier protein-2 (AeSCP-2), AeSCP-2 polypeptides and methods of their use.

BACKGROUND OF THE INVENTION

Insects are the most abundant form of animal life on the planet. From an industrial standpoint, insects are important due to their ability to transmit diseases and their role as agricultural pests. Therefore, efficient and safe insecticides are in great demand. One promising area of research in insecticides is the difference between fat metabolism in insects and animals. Animals and insects differ in the manner in which they obtain and use cholesterol. Vertebrates synthesize cholesterol while insects must obtain cholesterol from their diet. In contrast, insects have an absolute requirement for cholesterol in their diets. Fat metabolism in insects is thus a major target for development of agents with insecticidal activities.

Accordingly, there exists a need for the identification and characterization of fat metabolism-associated factors, such as the invention disclosed herein, that have a present benefit of being useful to screen compounds for fat metabolism altering activity. In particular, there is a distinct need for identification and characterization of such factors to identify compounds with cholesterol uptake inhibiting activity to act as insecticides. Furthermore, identification and characterization of such factors and their antagonists and agonists will provide new avenues to preventing, ameliorating or correcting cholesterol uptake-related dysfunction and disease in other organisms, including humans. It is envisioned that development of cholesterol uptake inhibitors in insect systems will also lead to the identification and refinement of new inhibitors of corresponding human proteins useful in blocking cholesterol uptake to prevent, for example, obesity.

SUMMARY OF THE INVENTION

In one embodiment, the present invention provides an isolated and purified polypeptide that is at least 85% identical to the AeSCP-2 amino acid sequence set forth in SEQ ID NO:3 or a fragment thereof which encodes a biologically active polypeptide capable of intracellular cholesterol transport in mosquitoes. In a preferred embodiment, the isolated and purified polypeptide is identical to the AeSCP-2 amino acid sequence set forth in SEQ ID NO:3.

The invention is also directed to an isolated and purified nucleic acid comprising a nucleotide sequence encoding the amino acid sequence set forth in SEQ ID NO:3 or fragments thereof which encode a biologically active polypeptide capable of intracellular cholesterol transport in mosquitoes. In a preferred embodiment, the isolated and purified nucleic acid has the nucleotide sequence set forth in SEQ ID NO: 1.

The invention also encompasses an isolated and purified nucleic acid that specifically hybridizes under stringent conditions to either strand of a denatured, double-stranded nucleic acid encoding an amino acid sequence set forth in SEQ ID NO:3. In preferred embodiments, the invention provides an isolated and purified nucleic acid that specifically hybridizes under stringent conditions to either strand of a denatured, double-stranded nucleic acid having the nucleotide sequence set forth in SEQ ID NO: 1.

In certain embodiments, the invention is an expression vector comprising an isolated nucleic acid according to the invention where the isolated nucleic acid is in operative association with one or more regulatory elements. The invention further provides a transformed host cell or organism comprising an isolated nucleic acid or expression vector as described herein.

The invention also encompasses a method of preparing an isolated polypeptide comprising AeSCP-2 or fragments thereof, comprising the step of culturing a transformed host cell or organism described herein under conditions conducive to expression of the polypeptide, and recovering the expressed polypeptide from the cell or organism in isolated form.

In yet another embodiment, the present invention provides a method of identifying whether a compound is an antagonist of AeSCP-2 biological activity, comprising the step of incubating an AeSCP-2 polypeptide or biologically-active fragment thereof with a biological target in the presence of a compound and measuring the ability of the compound to block the interaction between the AeSCP-2 or fragment and the biological target to thereby identify an antagonist effective in reducing AeSCP-2 biological activity. In preferred embodiments, the biological target is cholesterol.

As well, the present invention also provides a method of identifying whether a compound is an agonist of AeSCP-2 biological activity, comprising the step of incubating an AeSCP-2 polypeptide or biologically-active fragment thereof with a biological target in the presence of a compound and measuring the ability of the compound to increase the interaction between the AeSCP-2 or fragment and the biological target to thereby identify an agonist effective in increasing AeSCP-2 biological activity. In preferred embodiments, the biological target is cholesterol.

In other embodiments of the invention, there are provided methods for identifying compounds which bind to or otherwise interact with an AeSCP-2 polypeptide or fragment thereof comprising the steps of: contacting an AeSCP-2 polypeptide or fragment thereof with a compound to be screened under conditions to permit binding to or other interaction between the compound and the AeSCP-2 polypeptide or fragment to assess the binding to or other interaction with the compound, such binding or interaction being associated with a detectable signal in response to the binding or interaction of the polypeptide or fragment with the compound; and determining whether the compound binds to or otherwise interacts the AeSCP-2 polypeptide or fragment by detecting the presence or absence of the signal generated from the binding or interaction of the compound with the AeSCP-2 polypeptide or fragment.

Other objects, features and advantages of the present invention will become apparent after review of the specification, claims and drawings.

BRIEF DESCRIPTION OF THE DRAWINGS

FIG. 1. DNA sequence of AeSCP-2 complete cDNA (SEQ ID NO:2). The coding region (SEQ ID NO:1) is in capital case and the untranslated regions are in lowercase. Amino acid sequence (SEQ ID NO:3) is under the nucleic acid sequence and the sterol transfer domain is presented in bold letters. The starting codon and stop codons are underlined.

FIG. 2. Amino acid sequence alignment of members of SCP-2 gene family with AeSCP-2 (BQ785056; herein, SEQ ID NO:3). Human SCP-2 (NM_002979) (SEQ ID NO:6). Rat SCP-2 (M57454) (SEQ ID NO:5). Anopheles gambiae SCP-2 (EAA08376) (SEQ ID NO:4). Fruit fly C-terminal portion of SCP-X (X97685) (SEQ ID NO:7), CG11151 gene product (AE003493) (SEQ ID NO:8) and CG12296 (AE003724) (SEQ ID NO:9). Yeast PXP-18 (D86472) SEQ ID NO:11) and C. elegans UNC-24 C-terminal portion (U42013) (SEQ ID NO:10). Consensus sequence is from the NCBI conserved domain search (RPS-BLAST 2.2.3). Position of the amino acid is labeled at the left side of the sequences. Amino acids represented as "*" are the consensus sequence of the SCP-2 sterol transfer domain and additional amino acids important for the sterol transfer function (Stolowich et al., 2002) as "+". Identical amino acid sequences between AeSCP-2 and other SCP-2 are represented as "■". Gaps are introduced to maximize the alignment and are labeled as "–".

DETAILED DESCRIPTION OF THE INVENTION

I. In General

Figure 3:
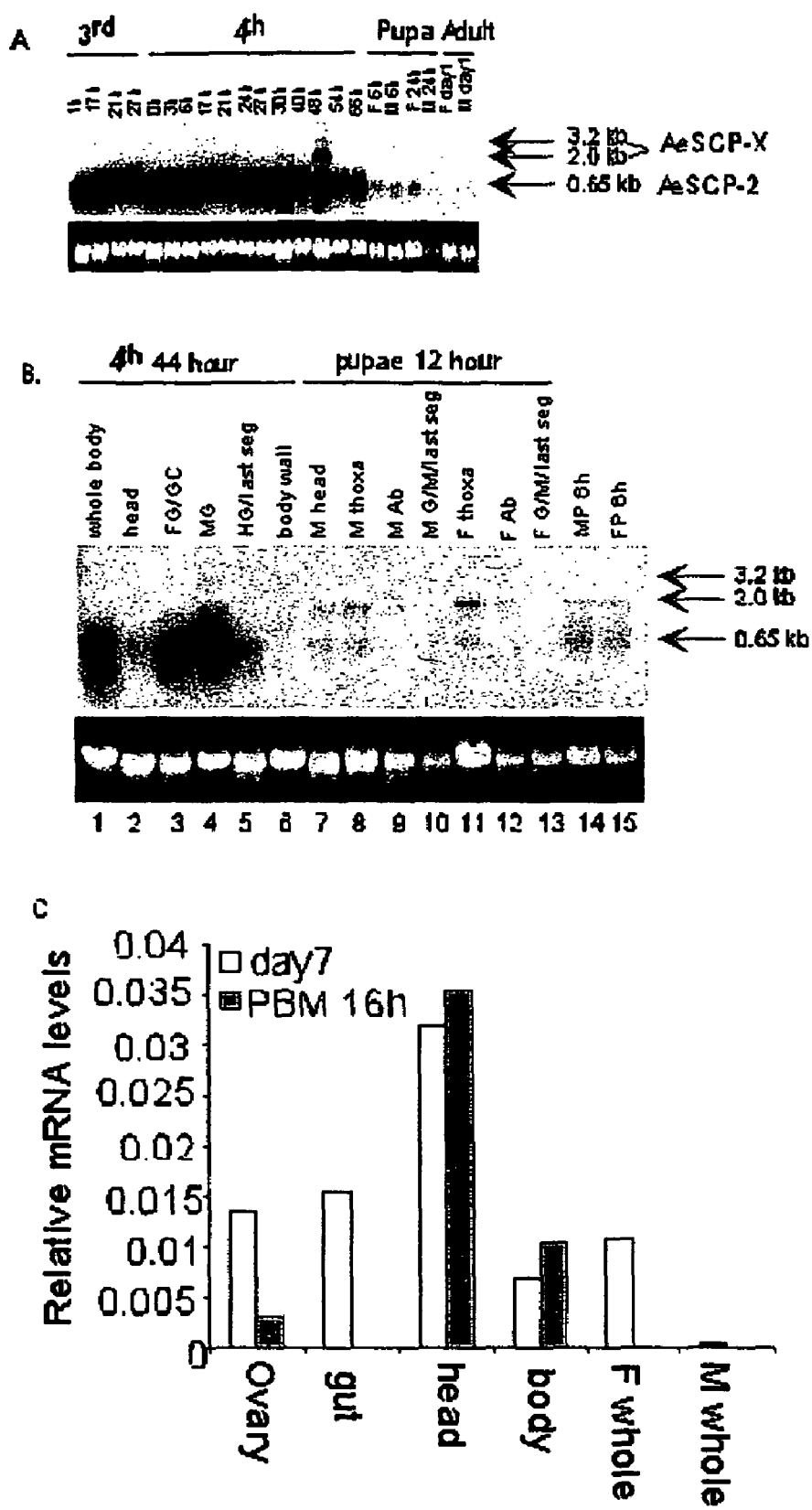
FIG. 3. Northern and dot blotting analyses of AeSCP-2 expression. A. Development expression profile of AeSCP-2 gene from 3rd instars to adults. The hour into each stadium is labeled as xh. B. Tissue distribution of AeSCP-2 transcripts in 4th instars and early pupae. FG=foregut. GC=gastric caeca (anterior midgut). MG=midgut. HG/M/last seg=hindgut/Malpighian tubes/last segment of abdomen. Body wall =epidermis, fat body, tracheae, muscle, peripheral nerves. PM=male pupae. PF=female pupae. C. Dot blotting analysis of relative AeSCP-2 MRNA levels in Day 7 adults. PBM=post blood meal. Gut tissues of blood-fed female were not used. Blank and hatched bars represent Day 7 females. Black bar=day 7 male. Relative MRNA level=levels of AeSCP-2 mRNAs normalized to 0 hour-old 4th instars that is arbitrarily set at 1. Ethidium bromide stain for the rRNA in the agarose gel is show under the northern blot image.

Before the present materials methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986).

II. The Invention

In one embodiment, the invention is directed to the polypeptide set forth in SEQ ID NO:3 (i.e., the mature polypeptide) as well as polypeptides and fragments, particularly those which have the biological activity of AeSCP-2, and also those which have at least 85% identity to a polypeptide of SEQ ID NO:3, and more preferably at least 90% identity to a polypeptide of SEQ ID NO:3, and still more preferably at least 95% identity to a polypeptide of SEQ ID NO:3.

A polypeptide fragment according to the invention is a polypeptide having an amino acid sequence that is entirely the same as part but not all of the amino acid sequence of the aforementioned polypeptides. AeSCP-2 polypeptide fragments may be "free-standing," or comprised within a larger polypeptide of which they form a part or region, most preferably as a single continuous region, a single larger polypeptide.

Preferred fragments include, for example, truncation polypeptides having a portion of an amino acid sequence of SEQ ID NO:3, or of variants thereof, such as a continuous series of residues that includes the amino terminus, or a continuous series of residues that includes the carboxyl terminus. Further preferred are fragments characterized by structural or finctional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically-active fragments which are those fragments that mediate activities of AeSCP-2, including those with a similar activity or an improved activity, or with a decreased undesirable activity. Particularly preferred fragments include fragments comprising domains that confer a function essential for viability of *A. aegypti* (e.g., the sterol transfer domain) or have the ability to initiate, maintain, or cause a dysfunction or disease in a mosquito or another organism expressing an AeSCP-2 counterpart, particularly a human. Particularly preferred fragments include those capable of cholesterol transport (defined herein as those fragments containing at least the amino acids making up the sterol transfer domain of AeSCP-2 and additional essential residues, as indicated in FIG. 1). Additional useful fragments are those fragments that are antigenic or immunogenic in an animal, especially in a human.

Variants that are fragments of the polypeptides of the invention may be employed for producing the corresponding full-length polypeptide by peptide synthesis; therefore, these variants may be employed as intermediates for producing the full-length polypeptides of the invention.

Another aspect of the invention relates to isolated polynucleotides, including the coding sequence that encodes the AeSCP-2 polypeptide having a deduced amino acid sequence of SEQ ID NO:3 and polynucleotides closely related thereto and variants thereof.

The DNA sequence set out in SEQ ID NO:1 contains an open reading frame encoding a protein having about the number of amino acid residues set forth in SEQ ID NO:3 with a deduced molecular weight that can be calculated using amino acid residue molecular weight values well known in the art. The polynucleotide of SEQ ID NO:2 includes the nucleotide sequence of SEQ ID NO: 1 and represents a complete determined sequence for an AeSCP-2 cDNA. In a preferred embodiment, the invention provides a polynucleotide sequence identical over its entire length to the coding sequence in SEQ ID NO:1.

AeSCP-2 of the invention is structurally related to other proteins of the SCP family as discussed further in the Example section below.

In addition to the coding sequence for the mature polypeptide or a fragment thereof, the invention also provides the coding sequence for the mature polypeptide or a fragment in reading frame with other coding sequence, such as those encoding a leader or secretory sequence, a pre-, or pro- or prepro-protein sequence. The polynucleotide may also contain noncoding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al, Proc. Natl. Acad. Sci., USA 86: 821–824 (1989), or an HA tag (Wilson et al., Cell 37: 767 (1984). Polynucleotides of the invention also include, but are not limited to, polynucleotides comprising a structural gene and its naturally associated sequences that control gene expression.

The term "nucleotide sequence encoding an amino acid sequence," as used herein, encompasses polynucleotides that include a sequence encoding a polypeptide of the invention, most particularly an AeSCP-2 polypeptide of *A. aegypti* having an amino acid sequence set out in SEQ ID NO:3. The term also encompasses polynucleotides that include a single continuous region or discontinuous regions encoding the polypeptide (for example, interrupted by integrated phage or an insertion sequence or editing) together with additional regions, that also may contain coding and/or non-coding sequences.

The invention further relates to variants of the polynucleotides described herein that encode for variants of the polypeptide having a deduced amino acid sequence of SEQ ID NO:3. Variants that are fragments of the polynucleotides of the invention may be used to synthesize full-length polynucleotides of the invention.

Further particularly preferred embodiments are polynucleotides encoding AeSCP-2 variants that have the amino acid sequence of the AeSCP-2 polypeptide of SEQ ID NO:3 in which several, a few, 5 to 10, 1 to 5, 1 to 3, 2, 1 or no amino acid residues are substituted, deleted or added, in any combination. Especially preferred among these are silent substitutions, additions and deletions, that do not alter the properties and activities of Ae-SCP-2, particularly the proteins ability to transport cholesterol.

Further preferred embodiments of the invention are polynucleotides that are at least 70% identical over their entire length to a polynucleotide encoding AeSCP-2 polypeptide having an amino acid sequence set out in SEQ ID NO:3, and polynucleotides that are complementary to such polynucleotides. Alternatively, preferred are polynucleotides that comprise a region that is at least 80% identical over its entire length to a polynucleotide encoding AeSCP-2 polypeptide (SEQ ID NO:3) and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred, and among these those with at least 98% and at least 99% are particularly highly preferred, with at least 99% being the more preferred.

Preferred embodiments are polynucleotides that encode polypeptides that retain substantially the same biological function or activity as the mature polypeptide encoded by a DNA of SEQ ID NO:1.

The invention further relates to polynucleotides that hybridize to the herein above-described sequences. In this regard, the invention especially relates to polynucleotides that hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5.times. Denhardt's solution, 10% dextran sulfate, and 20 micrograms/ml denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring arbor, N.Y., (1989), particularly Chapter 11 therein.

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989). Introduction may be by way of, but not limited to, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as *streptococci, staphylococci, enterococci E. coli, Streptomyces* and *Bacillus subtilis* cells; fingal cells, such as yeast cells and *Aspergillus* cells; insect cells such as *Drosophila* S2 and *Spodoptera* Sf9 cells; animal cells such as CHO, COS, HeLa, C127, 3T3, BHK, 293 and Bowes melanoma cells; and plant cells.

A great variety of expression systems can be used to produce the polypeptides of the invention. Such systems utilize vectors including, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or finctional mimetics. See, e.g., Coligan et al., Current Protocols in Immunology 1(2): Chapter 5 (1991).

In this aspect, the invention provides a method of screening compounds to identify those which enhance (agonist) or block (antagonist) the biological activity of AeSCP-2 polypeptides or polynucleotides, particularly those compounds that are affect cholesterol uptake and trafficking. In preferred embodiments, "biological activity" includes at least the cholesterol binding and transport properties of AeSCP-2. The method of screening may involve high-throughput techniques. For example, to screen for agonists or antagoists, a synthetic reaction mix, a cellular compartment, such as a membrane, cell envelope or cell wall, or a preparation of any thereof, comprising AeSCP-2 polypeptide and a labeled substrate or ligand of such polypeptide is incubated in the absence or the presence of a candidate molecule that may be a AeSCP-2 agonist or antagonist. The ability of the candidate molecule to agonize or antagonize the AeSCP-2 polypeptide is reflected in decreased/increased binding of the labeled ligand by the AeSCP-2 polypeptide. Molecules that bind gratuitously to the AeSCP and reduce the ability of labeled ligand or substrate to bind AeSCP are most likely to be good antagonists. Molecules that increase the rate of cholesterol uptake or increase the binding coefficient of labeled substrate or ligand are most likely agonists. Detection of the rate or level of labeled substrate or ligand binding may be enhanced by using a reporter system. Reporter systems that may be useful in this regard include but are not limited to colorimetric labeled substrate converted into product, a reporter gene that is responsive to changes in AeSCP-2 polypeptide activity, and binding assays known in the art (e.g., cholesterol binding assays as described in the Example section below).

Another example of an assay for AeSCP-2 antagonists is a competitive assay that combines AeSCP-2 and a potential antagonist with AeSCP-2 natural substrates or ligands, or substrate or ligand mimetics, under appropriate conditions for a competitive inhibition assay. For example, cholesterol can be labeled, such as by radioactivity or a colorimetric compound, such that the number of cholesterol molecules bound to a AeSCP-2 can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that binds the same sites as a natural ligand or substrate, such as cholesterol, thereby preventing the transport function of AeSCP-2 by excluding cholesterol from binding. Thus, potential antagonists include a small molecule that binds to and occupies the binding site of the polypeptide thereby preventing binding to natural substrates and ligands, such that normal biological activity is prevented. Examples of small molecules include but are not limited to small organic molecules, peptides or peptide-like molecules. Other potential antagonists include antisense molecules (see Okano; J Neurochem. 56: 560 (1991); OLIGODEOXYNUCLEOTIDES AS ANTISENSE INHIBITORS OF GENE EXPRESSION, CRC Press, Boca Raton, Fla. (1988), for a description of these molecules).

Each of the DNA sequences provided herein may be used in the discovery and development of insecticides. The encoded protein, upon expression, can be used as a target for the screening of compounds having potential insecticidal activity. In particular, high throughput screening of chemical banks may be carried out by screening techniques, preferably automated screening techniques, known in the art. Additionally, the DNA sequences encoding the amino terminal regions of the encoded protein or other translation facilitating sequences of the respective MRNA can be used to construct anti-sense sequences to control the expression of the coding sequence of interest.

As can now be appreciated, the invention also provides the use of an antagonist, also termed inhibitor, to interfere with the physical interaction between AeSCP-2, or related SCP proteins, and cholesterol molecules during fat metabolism. In particular, the reduction or disturbance of this interaction in insects will yield a broad-spectrum insecticidal method. It is also envisioned that certain antagonists identified as antagonists of AeSCP-2 will be effective in preventing cholesterol uptake in other organisms, most preferably humans. Such a method would provide an avenue for the treatment of obesity, an ever increasing problem in modern society.

The following definitions are provided to facilitate understanding of certain terms used frequently herein.

In addition to further definition herein, the term "fragment" is meant to encompass a portion of the AeSCP-2 protein or polypeptide; or a nucleotide sequence described herein which is at least approximately 15 contiguous nucleotides to at least approximately 50 contiguous nucleotides or longer in length. Such fragments are useful as probes for diagnostic purposes, experimental tools, or in the case of nucleic acid fragments, as primers. A preferred embodiment includes primers and probes which selectively hybridize to the nucleic acid constructs encoding the AeSCP-2 protein. For example, nucleic acid fragments which encode any one of the domains described herein are also implicated by the claimed invention.

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215: 403–410 (1990). The BLAST X program is publicly available from NCBI and other sources (BLAST Manual, Altschul, S., et al, NCBI NLM NIH Bethesda, Md. 20894; Altschul, S., et al., J. Mol. Biol. 215: 403–410 (1990). The well known Smith Waterman algorithm may also be used to determine identity.

"Isolated" or "purified" or "isolated and purified" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, PROTEINS—STRUCTURE AND MOLECULAR PROPERTIES, 2nd Ed., T. E. Creighton, W. H. Freeman and Company, New York (1993) and Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., Meth. Enzymol. 182:626–646 (1990) and Rattan et al., Protein Synthesis: Posttranslational Modifications and Aging, Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Variant" or "derivative" or "modification" as the terms are used herein, are a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed herein. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

The following Examples are offered by way of illustration and not by way of limitation.

III. Examples

A. Introduction

In insects, cholesterol is needed for cellular membranes and ecdysteroid biosynthesis. All insect cellular membranes contain cholesterol (Lasser and Clayton, 1966). Many studies have determined that the precursor of ecdysteroid biosynthesis is cholesterol, demonstrating that [$^3$H]cholesterol was converted to [$^3$H]ecdysteroids (Borovsky et al., 1986; Grieneisen et al., 1991). Yet, insects do not synthesize cholesterol de novo and depend on dietary and/or symbiotic microbes to provide cholesterol for their physiological needs (Clayton, 1964; Noda et al., 1979; Ritter and Nes, 1981; Dwivedy and Shukla, 1982; Nes et al., 1997).

Much has been done regarding the dietary requirement of sterols in insects, such as Heliothis zea (Ritter and Nes, 1981; Kuthiala and Ritter, 1988a; Nes et al., 1997), Manduca sexta (Svoboda and Weirich, 1995), and Pieris brassicae (Beydon and Lafont, 1987). Results from previous studies have revealed exquisite details on the cholesterol metabolic pathway, especially regarding ecdysteroid biosynthesis (Gilbert et al., 2002). Only a few proteins are known to be involved in cholesterol transport/metabolism, such as the hemolymph lipophorin (Soulages and Brenner, 1991; Jouni et al., 2002) and lipoprotein (Bianchi and Capurro, 1991). Nothing is known about the molecules involved in sterol transfer/conversion in the midgut of insects.

Intracellular transportation of cholesterol has to meet three important biological needs: absorb free cholesterol for the construction of cellular membranes, transfer cholesterol to peroxisome for catabolization, and provide cholesterol as a precursor to mitochondria for the steroid biosynthesis. These three pathways most likely utilize the same intracellular transport protein(s) to mobilize cholesterol. Based on vertebrate studies, the known elements of cholesterol intracellular trafficking machinery include clathrin-coated pits, scavenger receptor type B1, caveolae, phospholipid rafts, Niemann-Pick C disease protein, sterol carrier protein 2 (SCP-2), multidrug resistance protein, microsomal triglyceride transfer protein and steroidogenic acute regulation protein (Sviridov, 1999; Schroeder et al., 2001). One protein that can function in both the intracellular cycling of cholesterol and in transfer of cytosol sterol into mitochondria is SCP-2 (Gallegos et al., 2001). The biological importance of SCP-2 in cholesterol trafficking is deduced from the knockout mice that show moderately decreased level of cholesterol absorption by intestine and severally reduced bile salt formation (Fuchs et al., 2001) and symptom related to peroxisomal deficiency (Seedorf et al., 1998). In yeast, SCP-2 homolog, PXP18, is speculated to play a role in the beta-oxidation of long-chain fatty acids and may function as a molecular chaperone in peroxisomes (Tan et al., 1990, Bun-ya et al., 2000). In nematodes, a putative SCP-2 gene, UNC-24, is essential for the placement of UNC-1 in the cell membrane and organization of lipid rafts (Sedensky et al., 2001).

SCP-2 was first isolated as a cholesterol transporter involved in cholesterol and lipid intracellular trafficking in vertebrates (Seedorf et al., 2000; Gallegos et al., 2001). SCP-2 belongs to a family of proteins containing a sterol carrier domain, also known as the SCP-2 domain, which is named as the SCP-2 gene family. The SCP-2 gene family includes SCP-2, SCP-X, 17 beta-hydroxysteroid dehydrogenase Type IV, Metallo-beta-lactomase and stomatin (Gallegos et al., 2001; NCBI, 2002). In vertebrates, SCP-2 and SCP-X share exactly the same nucleotide sequences of SCP-2 domains because they are transcribed from the same gene (SCP-2/SCP-X gene). Other members of the SCP-2 gene family have a SCP-2 domain at the C-terminus of the protein but the nucleotide sequences of those SCP-2 domains are different significantly from the SCP-2/SCP-X gene (Seedorf et al., 2000; Gallegos et al., 2001). Several aspects of vertebrate SCP-2 are well known. Firstly, SCP-2 is an important component of sterol metabolism and steroid biosynthesis in vertebrates (Pfeifer et al., 1993a; review by Gallegos et al., 2001). Secondly, SCP-2 is demonstrated to bind to cholesterol, fatty acid, and fatty acyl CoA (Gallegos et al., 2001; Stolowich et al., 2002) and the affinity for different ligands is in the order: cholesterol>>straight chain fatty acid>kinked chain fatty acid (Schroeder et al., 2000). Thirdly, SCP-2 has been shown to accelerate conversion of cholesterol to steroids in mitochondria by increase the influx of cholesterol into mitochondria (van Noort et al., 1988; Xu et al., 1991). Fourthly, SCP-2 enhances sterol cycling between microsome and plasma membrane (Baum et al., 1997). Fifthly, tissues involved in either metabolism of cholesterol or steroid biosynthesis show high levels of SCP-2 expression (Baum et al., 1993; review by Gallegos et al., 2001).

The inventors provide herein a putative intracellular sterol carrier protein in *Aedes aegypti*, AeSCP-2 (BQ785056), the first found in insects. The homology of AeSCP-2 to SCP-2 of vertebrates in the conserved sterol transfer domain is 69%. Whether AeSCP-2 has parallel function as its vertebrate SCP-2 family members has not been reported. AeSCP-2 expressed at high levels in the midgut of 4th instars. Ligand-binding assays were performed to assess whether AeSCP-2 interacted with cholesterol specifically. The results suggest that AeSCP-2 has high affinity to cholesterol and functions as a carrier protein in mosquitoes.

B. Results

A 4th instar subtracted cDNA library enriched for transcripts of larval stage-specific genes was constructed (Krebs et al., 2002). Clone Ae4-339 (BQ785056) is a partial cDNA of 521 bp long that encompasses 1 complete open reading frame (ORF) of a 110 aa protein. The complete cDNA obtained by 5'RACE is 541 bp long (FIG. 1). The cDNA sequence of clone Ae4-339 was deposited into the NCBI EST databank on Jul. 26, 2002 under accession number BQ785056 (Ae4-339 4th instar subtracted cDNA library *Aedes aegypti* cDNA clone Ae4-339 3', mRNA sequence; version BQ785056.1 GI: 21993528). The complete cDNA of AeSCP-2 was deposited into the NCBI GenBank nucleic acid databank on Feb. 9, 2003 under accession number AY1 90283 (*Aedes aegypti* sterol carrier protein 2 mRNA, complete cds.; version AY190283.1 GI:28274795). Unmodified predicted protein has a mass of about 12.3 kDa. The protein has 30% identity and 55% similarity to the sterol carrier protein-2 of rat, and is of 46% identity and 69% similarity to the sterol-transfer domain of the sterol carrier protein-2 family from mammals (FIG. 2, amino acids indicated with "*"). Amino acids that are important for SCP-2's sterol transfer function are conserved in AeSCP-2 (FIG. 2, amino acids indicated with "+"). AeSCP-2 also shows a 50% similarity to a SCP-2-like gene (XM_115847.1) in the human genome. AeSCP-2 has a 79% identity and 90% similarity to *Anopheles gambiae* gene EAA08376 (FIG. 2). AeSCP-2 has over 25 to 38% identity and 52% similarity to three *Drosophila* genes, CG11151 (AE003493), CG12269 (AE003724), and the C-terminal portion of SCP-X (X97685). SCP-X is a fusion protein of a thiolase and SCP-2 at the C-terminus (Ossendorp et al., 1990; review by Mannaerts et al., 2000). SCP-X is involved in metabolism of long chain fatty acids. In yeast and *C. elegans*, SCP-X and SCP-2 are two separated genes (Pfeifer et al., 1993a). The sterol transfer domain of AeSCP-2 shows 35% and 54% similarity to *Caenorhabditis elegans* (U42013) and yeast (D86472), respectively (FIG. 2). The vertebrate SCP-X/SCP-2 gene is transcribed from a single copy gene that has two promoters controlling the transcription of SCP-X and SCP-2 with several alternative transcription start sites (Seedorf and Assmann, 1991; Ohba et al., 1995).

In the 4th stadium, probes of AeSCP-2 cDNA detected 3 transcripts of 3.2, 2.0 and 0.65 kb (FIG. 3A), which potentially code for SCP-X and SCP-2 (see discussion). The AeSCP-2 mRNA is the 0.65 kb (FIG. 3A). ). The molecular weight difference between AeSCP-2 mRNA and the complete cDNA (541 bp) could be a result from poly(A)n tails in the mRNA. AeSCP-2 was expressed strongly throughout tested larval stages and decreased to low levels after pupation (FIG. 3A). AeSCP-2 is expressed in the 1 st instars as well (data not shown). Interestingly, tissues that expressed AeSCP-2 strongly were midgut and possibly foregut (FIG.

3B, lanes 4 and 3). There were low levels of AeSCP-2 mRNA detected in the head and hindgut as well (FIG. 3B, lanes 2 and 5). However, the transcripts were extremely low in the body wall that includes epidermis, fat body, muscles, tracheae and peripheral nerves (FIG. 3B, lane 6).

Figure 4:
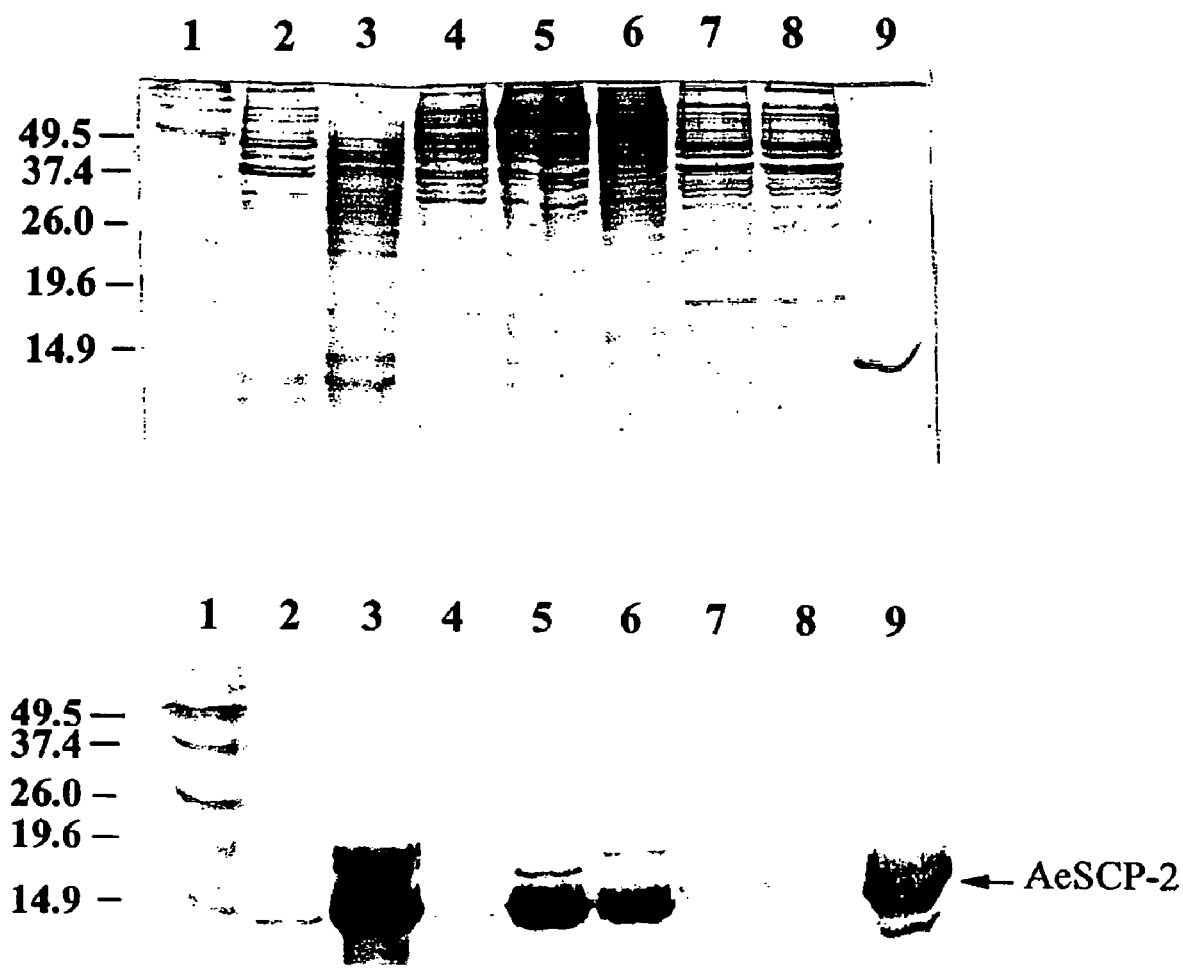
FIG. 4. Western blotting analysis of AeSCP-2. Proteins from animals were. loaded 20 ug per lane. Lane 1: protein size marker. Lane 2: the head of Day 2 4th instars. Lane 3: the gut of Day 2 4th instars. Lane 4: the body wall of Day 2 4th instars. Lane 5: the Day 1 female pupae. Lane 6: Day 1 male pupae. Lane 7: Day 7 female adults. Lane 8: Day 7 male adults. Lane 9: recombinant AeSCP-2. Upper panel is the 15% SDS PAGE protein stained with Commassie blue G-250 solution. The lower panel is the western blot using rabbit anti-AeSCP-2 antibody (1:1000 dilution).

Analyses of AeSCP-2 profiles using polyclonal anti-AeSCP-2 antibodies showed that the protein levels reflected the transcription of AeSCP-2 gene. High level of AeSCP-2 was only observed in the gut tissue of larvae (FIG. 4, lane 3). AeSCP-2 in extracted protein sample was of the predicated molecular weight of 13 kDa (FIG. 4, lanes 2–8). However, it is noticed that minor bands of 17 to 19 kDa were observed in western blotting analysis (FIG. 4, lanes 3, 5, and 6), which were of higher molecular weight than predicated from the AeSCP-2. ORF. Those higher molecular weight proteins might be either modified AeSCP-2 or related proteins that cross-react with anti-AeSCP-2 antibodies. Very faint bands of 42 kDa and higher molecular weight proteins were observed in western blot (FIG. 4C, lane 2-8), which might include the AeSCP-X (FIGS. 3A and B).

AeSCP-2 transcripts were observed at equal levels in the first day adults of both sexes (FIG. 3A), by day 7, only females continued to have detectable transcription (FIG. 3C, blank and solid bars of whole animals). At the protein level, SCP-2 was detected in both day 7 females and males (FIG. 4, lane 7 and 8). All tested tissues showed low levels of SCP-2 gene transcription in day7 females and the head seemed to have slightly higher levels (FIG. 3C). Interestingly, AeSCP-2 MRNA level decreased more than 4-fold in the ovary 16 hours post-blood meal but in the head the levels remained the same as none-blood fed females of the same age (FIG. 3C).

Figure 5:
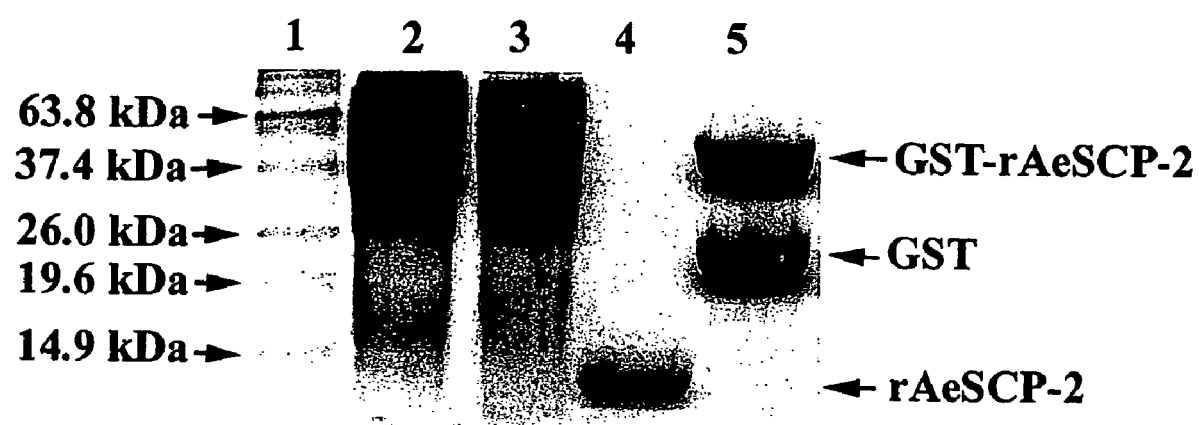
FIG. 5. Purification of recombinant AeSCP-2. Lane 1: protein molecular weight marker. Lane 2: supernatant of bacterial lysate. Lane 3: flow through of supernatant on a GST column. Lane 4: flow through after Thrombin digest in the GST column. Lane 5: elutant with glutathion. Protein samples was analyzed on 15% SDS PAGE and stained with Commassie blue dye.
Figure 6:
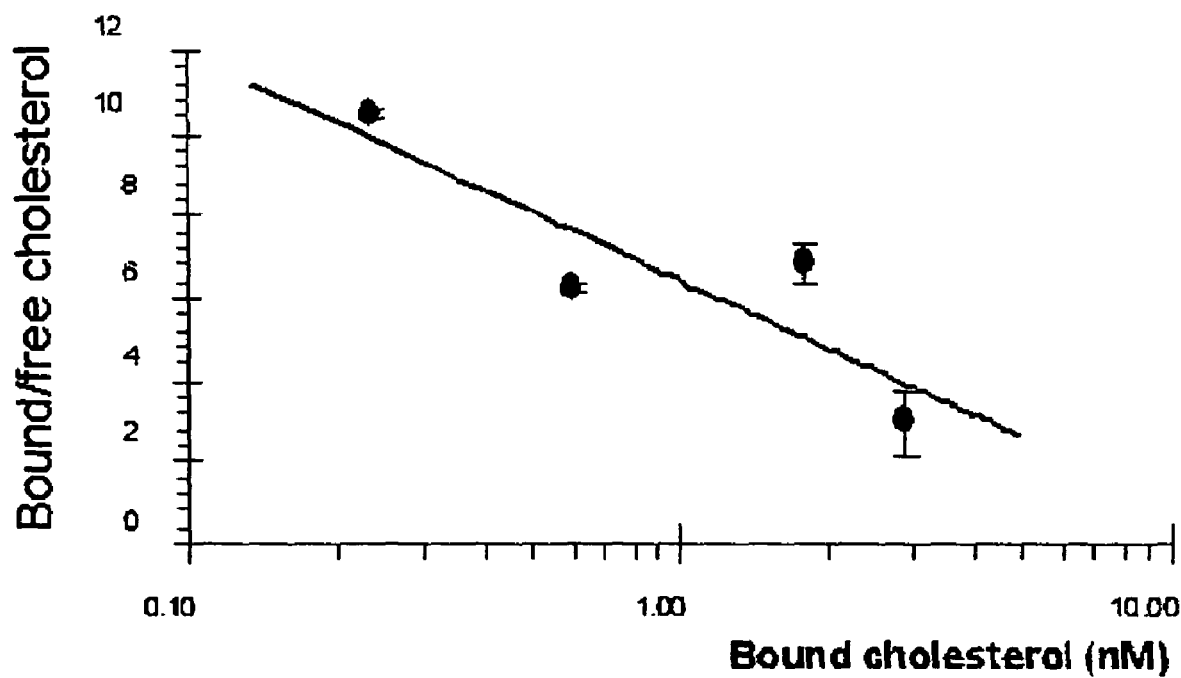
FIG. 6. Binding of radiolabeled cholesterol to recombinant AeSCP-2. Scatchard plot of [bound/free] cholesterol vs. molarity of bound cholesterol is shown. Values represent the average of 2 assays each with an N =3. Bars=standard deviation.

Whether AeSCP-2 binds cholesterol with high affinity was examined using radiolabeled cholesterol and recombinant AeSCP-2 (rAeSCP-2). Lipidex-1000 has been used for studying lipid/sterol binding proteins over decades and is proven to be a reliable assay (Glatz and Veerkamp, 1983; Colles et al., 1995). The recombinant protein was purified as GST-tagged fusion protein (FIG. 5, lanes 2 and 5) on the GST affinity column and the GST-tag was removed using Thrombin (FIG. 5, lane 4). After 16-hour Thrombin digest, there was still considerable amount of uncut fusion proteins (FIG. 5, lane 5) that may be resulted from insufficient concentration of Thrombin in the column (400 units/10 ml column). Further digest with increased level of Thrombin did completely remove the GST tag (data not shown). To optimize the condition for binding assay, varied concentrations of rAeSCP-2 was tested with 0.07 to 0.1 pM of radiolabeled cholesterol per assay. Protein concentration of 8 pM per assay reaction was chosen as the optimal testing condition for competition assays because it was the minimal concentration of protein that bound most of the radiolabeled cholesterol (data not shown). Scatchard plot analysis of [$^3$H]cholesterol binding to AeSCP-2 yielded a $K_d$ of $5.5 \pm 0.6 \times 10-9M$ (N=6), which indicate AeSCP-2 has high affinity to cholesterol (FIG. 6).

To investigate whether ecdysteroids affect AeSCP-2 expression, 12 hour-old 4th instars were dissected to separate the head, gut, and carcass. Gut and carcass were cultured in the same dish with and without 20E (60 ng/ml) for 6 hours. Results from tissue cultures showed that 20E (60 ng/ml) increased the levels of MRNA by 2-fold in cultured gut but not in the carcass (FIG. 7A). As expected, at the protein level AeSCP-2 increased in 20E-treated gut tissue cultures (FIG. 7A, inset, lane 5).

C. Discussion

AeSCP-2 is a member of the SCP-2 gene family (FIG. 1). The only other SCP-2 family member described in insects is the *Drosophila* SCP-X (X97685). Unexpectedly, the amino acid sequence similarities between AeSCP-2 and the SCP-2 domain in *Drosophila* SCP-X are not very high (52%, FIG. 2). *Drosophila* CG11151 gene is named as fly esterodial 17 beta dehydrogenase (FlyBase, 2001). However, the sequence lacks a dehydrogenase domain (Seedorf et al., 1995). CG11151 gene is most likely a *Drosophila* SCP-2-like gene. There is no information on the tissue and expression profiles of GC11151 gene in *Drosophila* (FlyBase, 2001). No mutant of the *Drosophila* CG11151 gene exists and its function is undetermined.

The multiple MRNA species detected using SCP-2 cDNA probes under high stringency is likely for SCP-X and SCP-2, respectively. The inventors speculate that the 2.0 and 3.2 kb MRNA (FIG. 3) were the transcripts for AeSCP-X because SCP-X is the only known transcripts containing SCP-2 sequence at the 3' of the ORFs in *Drosophila* (Kitamura et al., 1996) and in vertebrates (review by Gallegos et al., 2001). Vertebrate SCP-X/SCP-2 is transcribed from a single copy of gene that has two promoters controlling the transcription of SCP-X and SCP-2 (Seedorf and Assmann, 1991; Ohba et al., 1995). ). In rat, SCP-X/SCP-2 is transcribed from a single copy of gene, produces 4 transcripts (0.8, 1.4, 2.1 and 2.7 kb mRNAs). The 0.8 and 1.4 kb mRNAs translate into SCP-2 and pro-SCP-2; and 20 amino acids in the N-terminus of pro-SCP-2 is cleaved to generate SCP-2 immediately of translation (review by Gallegos et al., 2001). The 2.1 and 2.7 kb transcripts produce the SCP-X protein (Seedorf and Assmann, 1991). However, it is noticed that *Drosophila* SCP-X only has a single transcript of 1.4 kb in the midgut of embryos (Kitamura et al., 1996). Whether *Drosophila* SCP-X gene transcribes both SCP-X and SCP-2 in later stages is unknown. In vertebrates, minor amount of SCP-2 protein is generated from SCP-X (58 kDa) by post-translational modification to generate the 46 kDa thiolase and the 13 kDa SCP-2. Therefore, it is possible that *Drosophila* SCP-X gene only makes a single transcript at transcription level and generate SCP-2 from SCP-X by post-translational modification.

Polyclonal anti-AeSCP-2 antibodies recognized a major protein of 13 kDa and very low amount of proteins of higher molecular weight (larger than 42 kDa) in all examined tissues (FIG. 4). The high molecular weight immunoreactive proteins could represent either SCP-X/other members of SCP-2 family or due to nonspecific interaction to the AeSCP-2 antibodies. The pre-immune serum did not recognize those proteins in a parallel western blotting analysis (data not shown). The immunoreactive proteins of 17 to 19 kDa in protein extracts might be modified AeSCP-2. Post-translational modification of SCP-2 has been reported in vertebrates, which produces SCP-2 with slightly high molecular weight (Steinschneider et al., 1989).

Insects do not synthesize cholesterol and have to obtain cholesterol from dietary source (Clayton, 1964; Gilbert, 1967). Therefore, absorbing and transporting cholesterol by digestive system of insects are very important physiological processes. The substantial physiological differences in cholesterol metabolism between insects and vertebrates are that insects have the tendency to accumulate cholesterol in the body during feeding stages (Beydon and Lafont, 1987; Feldlaufer et al., 1995; Jouni, et al., 2002) and they have very low rate of cholesterol catabolism (Ritter, 1984; 1986; Spates et al., 1988). The C-terminal of AeSCP-2 does not have the peroxisome targeting sequence (AKL or SKL) that is in vertebrate SCP-2 members (FIG. 2). AeSCP-2 may be involved in transfer of sterol between cellular compartments such as lysosomes (Gallegos et al., 2000), ER (Puglielli et al., 1995), plasma membrane (Baum et al., 1997) and mitochondria but not peroxisome. In larvae of *Heliothis zea*, cholesterol is rapidly transported from gut into the hemolymph and most of the cholesterol is associated with foregut and midgut (Kuthiala and Ritter, 1988b). AeSCP-2 expression pattern and tissue specificity (FIGS. 3A and B) is consistent with the notion that dietary cholesterol is absorbed in the midgut (Jouni et al., 2000).

Tissue distribution of AeSCP-2 changed through development. In larvae, AeSCP-2 transcription was at high and low levels in the gut and head, respectively (FIG. 3B). Fat body is known to store high levels of cholesterol (Jouni et al., 2002), the inventors expected to see moderate levels of AeSCP-2 expression in the body wall that includes epidermis, fat body, muscles, tracheae and peripheral nerves. The levels of transcripts were extremely low in the larval body wall (FIG. 3B, lane 6). However, SCP-2 was detectable by western blotting analysis (FIG. 4, lane 4). It seemed that functional AeSCP-2 was in the body wall that includes fat body. The low levels of AeSCP-2 expression in the larval body wall implies either cholesterol is only stored in those tissues with little intracellular exchanges between compartments or there is another protein instead AeSCP-2 that performs the sterol transfer function in those tissues. Broad tissue distribution of SCP-2 has been reported in vertebrates as well. In rat, the liver has higher levels of MRNA, and the 0.8 kb mRNA is the major transcript (Seedorf and Assmann, 1991). Other tissues also have detectable levels of SCP-X/SCP-2 transcription (van Heusden et al., 1990; Baum et al., 1993; McLean et al., 1989).

It is interesting that early pupae transcribed AeSCP-2 gene in the body wall of both thorax and abdomen (FIG. 3B, lanes 8, 9,11 and 12) in contrast to the very low level of mRNA in the body wall of larvae (FIG. 3B, lane 6). Because the CNS and ovaries were removed from the abdomen of female pupae, transcription of AeSCP-2 in the body wall of female pupal abdomen (FIG. 3B, lane 11 and 12) was contributed by tissue(s) other than CNS or ovaries. The 2.0 and 0.65 kb transcripts seemed at equal levels in pupae (FIG. 3B, lanes 1, 14 and 15). However, SCP-2 was detected at much higher amount than it was expected (FIG. 4, lane 5 and 6). It implies that SCP-2 mRNA might be translated more efficiently, or SCP-2 was more stable, or translated SCP-X was processed to generate SCP-2 and a thiolase that was not immunoreactive to the AeSCP-2 antibodies. Antibodies against the sterol transfer domain of rat SCP-2 detect two proteins, 58 kDa of SCP-X and 13 kDa of SCP-2; but the thiolase generated by SCP-X cleavage does not cross-react with SCP-2 antibodies (Gallegos et al., 2001).

The major pathway of exogenous cholesterol internalization is via the lysosomes (Schoer et al., 2000). SCP-2 is essential for steroid biosynthesis in vertebrate because it mediates sterol transfer from lysosomes and microsomes to mitochondria (Pfeifer et al., 1993b; Gallegos et al., 2000), where sterol synthesis occurs. It is hypothesized that AeSCP-2 expression occurs in steroidogenic tissues in mosquitoes as well. The inventors expected to detect moderate levels of AeSCP-2 transcription in tissues that produce ecdysteroids. The define ecdysteroidogenic tissue in adult females is the ovaries (Hagedorn et al., 1975) and there was considerable amount of AeSCP-2 transcript in ovaries of none-blood fed mosquitoes (FIG. 3C). This result implies that AeSCP-2 may play a role in ecdysteroid biosynthesis in ovaries of blood fed mosquitoes. Sterol transfer into mitochondria is one of the rate limiting steps in steroid biosynthesis and SCP-2 enhances the rate of cholesterol transfer from lysosomes into mitochondria (Gallegos et al., 2000). Ecdysteroid production in ovaries peaks at 24 hour post blood meal (Borovsky et al., 1986). It is possible that decrease of AeSCP-2 transcription at 16 hour post blood meal in ovaries is a mechanism to modulate ecdysteroid production. Transcriptional changes in levels and tissue distribution of SCP-2 mRNA is also reported in developing chicken, in which follicular maturation coincides with the decrease of SCP-2 transcription (Pfeifer et al., 1993a).

The strong ecdysteroidogenic tissues, namely the thorax and entire abdomen of larvae (Jinkens et al., 1992), had extremely low levels of SCP-2 transcript (FIG. 3B, lane 6) and very low amount of SCP-2 (FIG. 4, lane 4). It is possible that only very few limited cells in thorax and each segment of abdomen are capable of producing ecdysteroids and those cells do express SCP-2 gene. However, a few ecdysteroidogenic cells in abdomen may not be able to elevate the over all levels of SCP-2 transcripts to a high level. AeSCP-2 transcription was observed in the heads of larvae, pupae and day7 adult female (FIGS. 3B and C). Presence of SCP-2 in brain tissue especially in neurons has been described in vertebrates (Myers-Payne et al., 1996). SCP-2 is thought to be a multifunctional lipid/sterol carrier protein (Gallegos et al., 2001) and lipids/cholesterol are essential to brain function. Therefore, expression of AeSCP-2 in the head of mosquito larvae, pupae and adults is consistent with the potential function of this protein.

SCP-2 has been implicated in intracellular cholesterol transportation since it was discovered 3 decades ago (review by Gallegos et al., 2001). In the last 5 years many studies have showed that SCP-2 seemed multifunctional due to its ability to bind cholesterol (Schroeder et al., 2000), fatty acids (Frolov et al., 1996; Schroeder et al., 2000), and fatty acyl CoA (Frolov et al., 1996). SCP-2 extracted from liver did not have cholesterol or any lipid associated with the protein (Gallegos et al., 2001). Whether SCP-2 binds to cholesterol in vivo and how it functions, as a transporter, is a mystery. In vertebrates, results from SCP-2 cholesterol-binding studies have been controversial. The $K_d$ values of SCP-2 cholesterol-binding varied from 4 nM to 2.6 uM (Gallegos et al., 2001), which led to the conclusions either SCP-2 is an efficient cholesterol binding protein (Schroeder et al., 2000) or SCP-2 is not a functional cholesterol carrier (Seedorf et al., 2000). AeSCP-2 showed high affinity to cholesterol with a $K_d$ of $5.6 \times 10^{-9}$M, which implies that AeSCP-2 may function as a sterol carrier in mosquitoes.

Figure 7:
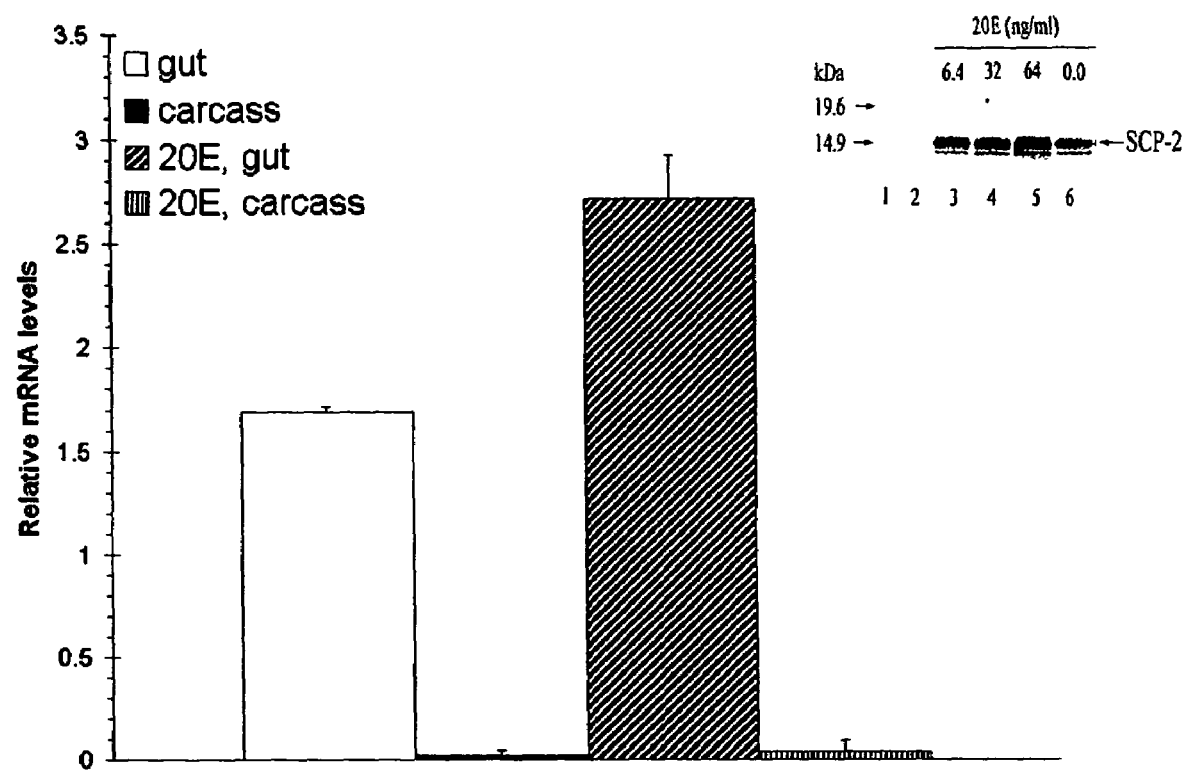
FIG. 7. Effects of 20E (60 ng/ml) on the expression of AeSCP-2 gene in cultured tissues from 12 hour-old 4th instars. Relative MRNA level=levels of AeSCP-2 mRNAs normalized to 0 hour-old 4th instars that is arbitrarily set at 1. Gut=complete digestive track. Body=carcass (muscle, tracheae, peripheral nerves, fat body, and CNS). Relative MRNA level: normalized to the level of mRNA of newly molted 4th instars, which is arbitrarily set at 1. Standard deviations are shown (N=3). Inset: the protein profiles of AeSCP-2 in 20E-treated cultured gut tissues. Lane 1: protein molecular size markers. Lane 2: body walls from 12 hour-old 4th instars after 6 hours in culture medium. Lane 3-5: guts from 12 hour old 4th instars after 6 hours in cultured medium containing 6.4, 32, and 64 ng/ml 20E, respectively. Lane 6: guts from 12 hour-old 4th instars after 6 hours in culture medium.

Reported peak of ecdysteroid titers in the hemolymph of *Aedes. aegypti* 4th instars was about 20 ng/ml (Jenkins et al., 1992). Addition of 60 ng/ml 20E in tissue cultures increased AeSCP-2 expression in the gut of 4th instars (FIG. 7; and FIG. 7 inset, lane 5). These results provide the first piece of evidence that ecdysteroids may directly regulate cholesterol uptake in the midgut of insects. This is not surprising because hormones affect SCP-2 transcription in vertebrates as well. Injection of estradiol into roosters causes a 2-fold increase of SCP-2 MRNA (Pfeifer et al., 1993a). Gonadotropins increase levels of SCP-2 MRNA in the ovarian (Rennert et al., 1991). It is highly possible that ecdysteroids modulate AeSCP-2 expression, which affect the absorption and distribution of cholesterol.

AeSCP-2 is the first putative intracellular cholesterol transporting protein reported in insects. The transcriptional profiles and tissue distribution of AeSCP-2 mRNA suggest that AeSCP-2 may be involved in cholesterol absorption/intracellular transfer and ecdysteroid biosynthesis. The results from direct binding of [³H]cholesterol showed that AeSCP-2 has high affinity to cholesterol. Thus, it provided strong evidence that AeSCP-2 functions as a cholesterol transporter in mosquitoes.

D. Experimental Procedures

Chemicals—Chemicals and reagent were purchased from Sigma (Sigma, St. Louis, Mo.), Fisher Scientific (Pittsburgh, Pa.) and ICN (Costa Mesa, Calif.) if their origins were not mentioned in the text. Lipidex 1000 (Type VI Hydroxy-alkoxypropyl Dextran) was purchase from Sigma. Radiolabeled [³H] cholesterol (40 Ci/mM) was purchased from ICN (ICN, Costa Mesa, Calif.).

Mosquitoes—The mosquitoes used in these experiments, Aedes. aegypti, are taken from an inbred laboratory strain (Rockefeller). Larvae were reared at 26° C. in 70–80% humidity with a light:dark (14:10) with pellets of rabbit food. Larvae hatching during a 15-minute period were collected and used in experiments. Under these conditions, development takes 64 hours (mostly males) to 72 hours (mostly females) to complete the 4th stadium. Adults were maintained at 24° C.

Pharate 4th instars were staged by its physical appearance: the visible dark black hairs of 4th stadium larva wrapped around the body under the thorax and abdominal cuticle of the 3rd instar (Christophers, 1960). Larvae selected by this criteria ecdyse during a 1 hour period. Pharate 4th instars were selected and transferred into a new container and newly molted 4th instar larvae were collected.

Pharate pupae were identified by their physical characters: a rudiment respiratory trumpets that turn dark brown on the anterior of the thorax under the cuticle of a late 4th instar, at which time pupation will happen within 1 hour (Christophers, 1960). Pharate pupae were transferred into a container and collected as newly molted pupae.

RNA extraction—Ten staged animals were washed with $ddH_2O$, rinsed once with $DEPC-H_2O$ and excess water was blotted off using clean Kimwipes. Cleaned animals were put into a 1.5 ml eppendorf test tube and homogenized with a micropestle in 1 ml of Trizol reagent according to the Manufacture's instruction (Invitrogen Corporation, Carlsbad, Calif.).

Tissues were dissected in insect saline solution (Riddiford et al., 1979) under dissecting microscope and put in 0.5 ml of Trizol reagent immediately. Once enough tissues were collected they were homogenized with a micropestle and another 0.5 ml of Trizol reagent was added into the test tube. The mRNA samples were frozen away at –80° C. until use. At least 20 animals were used to isolate different tissues at each time point.

PCR amplification of the 5' cDNA end—Two primers were designed for 5' rapid amplification of cDNA end (RACE) based on the partial cDNA sequence AeSCP-2. Primer-1 (5'-GTCGGACTTCGAGAGACA-3' (SEQ ID NO:12')) and primer-2 (5'-TTACTTCAGCGAGG-3' (SEQ ID NO:13)) match to the N-terminal and the C-terminal of the protein, respectively. The Smart RACE cDNA amplification Kit (ClonTech, Palo Alto, Calif.) was used for 5' RACE with cDNAs made from 24 hour-old 4th instars. The PCR products were cloned into the pT-Adv plasmid (ClonTech), transformed into E. coli DH5 alpha strain and plated on LB plates under Ampicillin selection. Plasmid minipreps of 4 clones containing inserts were made using QiaSpin column (QIAGEN, Valencia, Calif.) and sequenced in an automatic sequencer (ABI 377XL) using BigDye labeling (Amersham Pharmacia Biotech AB, Uppsala, Sweden).

Northern and dot blotting analysis—Fifteen to twenty microgram of total RNA from indicated stages was used in Northern blotting analysis as described (Ausubel et al., 1993). After electrophoresis, RNAs in the formaldehyde-agarose gel was blotted onto positively charged Nylon membrane (Millipore, Bedford, Mass.). For dot blotting analysis, 5 ug of total RNA from three parallel samples (10 larvae per sample) of each developmental time point were blotted on to positively charged Nylon membrane as described (Millipore). The membranes were baked at 80° C. under vacuum for 1 hour and UV cross-linked (Stratagene Cloning system, La Jolla, Calif.).

Radioactive probes were made using either 50 uCi [alpha-$^{32}$P] dATP (3000 Ci/mM) or [alpha-$^{32}$P] dCTP (3000 Ci/mM) with the PrimerIT II kit (Stratagene) or PCR reaction with DNA polymerase Tfl (Epicentre, Madison, Wis.). The PCR reaction was performed under 1 cycle of 94° C., 3 minute to denature the template, then 3 cycles of 94° C. for 2 minutes, 50° C. for 3 minutes and 72° C. for 5 minutes. The probes were cleaned using QiaSpin column (QIAGEN).

Membranes were prehybridized at 42° C. for at least 2 hours in a hybridization oven (Robbins Scientific, Sunnyvale, Calif.) in pre/hybridization solution (4×SSC, 10×Denhardt's solution, 50% formamide, 0.1% SDS, 50 mM $NaPO_4$ (pH 7.2), 1 mM EDTA and 100 ug/ml sheared herring sperm DNA). Denatured labeled cDNA probes were added in the prehybridization solution at more than $2-3×10^6$ cpm/ml and incubated at 42° C. overnight in the hybridization oven. The membranes were washed once each at 65° C. for 15 minutes in 2×SSC/0.1% SDS, 1×SSC/0.1% SDS, 0.5×SSC/0.1% SDS and 0.2×SSC/0.1% SDS. The membranes were exposed to a Phosphor image screen for at least 1 hour and scanned with a Storm 820 (Molecular Dynamics, Piscataway, N.J.). The data were analyzed using Storm 800 software.

Production of anti-AeSCP-2 bodies—To produce recombinant AeSCP-2 (rAeSCP-2), the entire coding region of the AeSCP-2 gene was cloned into the pGEX-4T GST tag vector (Amersham Pharmacia). Sequence analysis was performed to confirm that the fusion protein was in frame with GST. The GST/AeSCP-2 fusion protein was purified on a GST affinity column and the GST tag was removed by digesting with Thrombin according to the instruction with slight modification (Amersham Pharmacia). The bacterial culture was incubated overnight at 18° C. after addition of 0.2 mM IPTG (at the cell density of OD600=0.8) to prevent the formation of enclusion body-bound AeSCP-2. The predicted molecular weight of AeSCP-2 is 12.3 kDa and the purified rAeSCP-2 is 13 kDa estimated on the SDS-PAGE gel (FIG. 1, lane 4). Thrombin was removed from eluted rAeSCP-2 by passing through a benzamidine column (Amersham Pharmacia). The inventors were able to obtain 100 mg of the fusion protein from 2.5-liter cultures. Purified AeSCP-2 was concentrated to 8.1 mg/ml in phosphate saline buffer (PBS), pH 7.4, stored in PBS at –80° C. The purified AeSCP-2 was diluted in 10 mM K-phosphate buffer, pH 7.4, to desired concentrations (40 fM to 5 uM) for binding assay.

Purified rAeSCP-2 (8 mg/ml) was sent to the Polyclonal Antibody Service Laboratory (Clinic Science Center, University of Wisconsin—Madison, Madison, Wis.) for the production of polyclonal anti-AeSCP-2 antibodies in a rabbit. Pre-immune serum and anti-AeSCP-2 serum were tested against rAeSCP-2 by western blotting to ensure that high titer of AeSCP-2 antibodies was obtained.

Western blotting analysis—Intact animals, dissected tissues and cultured tissues were homogenized in lysis buffer (0.25M TRIS®HCl (hydroxymethyl aminomethane hydrochloride), pH 8.0/0.2% TRITON®X-100 (octyl phenol ethoxylate) 1 mM dithioerythritol/5 mM EDTA/10 mM β-mercaptoethanol/1 mM phenylmethylsulfonyl fluoride/ protease inhibitor cocktail (Sigma)), and centrifuged at 12000×g at 4° C. for 15 minutes. Supernatants containing solvable proteins were stored at −80° C. Protein concentrations were determined using a BCA kit (Pierce, Rockford, Ill.). Western blotting analysis was performed as described (Lan et al., 1999) using either SDS 15% PAGE or SDS 4–20% gradient PAGE (JSC BioExpress, Kaysville, Utah). The protein blots were incubated with 1:1500 dilution of rabbit polyclonal anti-AeSCP-2 antibodies. The goat anti-rabbit horseradish peroxidase conjugated secondary antibody (Jackson ImmunoResearch laboratory, West Grove, Pa.) was used at 1:3300 dilution. DAB solution (0.3 mg/ml and 0.03% hydrogen peroxide in PBS) was used to visualize the bound antibodies, which was developed within 5 minutes at room temperature.

Radiolabeled cholesterol binding assay—The binding of radiolabeled cholesterol to AeSCP-2 was measured based on the Lipidex-1000 assay (Glatz and Veerkamp, 1983) optimized for AeSCP-2. The Lipidex-1000 was prepared as follow: dry Lipidex-1000 was suspended in 50 volume of 1 N NaOH at room temperature for 30' with shaking, centrifuged at 2000×g for 10'. The pellet was washed once with 50 volume of propylene oxide, and then, twice with methanol to stripe off any bound lipid from the resin. The wet pellet was air dried at 50° C. Cleaned Lipidex-1000 was suspended and washed twice in 50 volume of 10 mM K-phosphate buffer (pH 7.4) to remove methanol. The suspension (50% v/v) was stored in 10 mM K-phosphate buffer containing 0.3% NaN.

Standard cholesterol solution was made from pure cholesterol (Sigma) in 95% ethanol at concentrations 0.04 nM to 20 uM. Two microliter of standard cholesterol was dispensed in the bottom of glass test tubes and ethanol was allowed to evaporate at room temperature. Then, 100 ul of diluted [$^3$H]cholesterol at about 0.1 pM in 10 mM K-phosphate buffer was added into the test tubes and the cholesterol solution was vortexed for 30". The final concentrations of unlabeled cholesterol per competition binding assay reaction were 0.08 pM to 40 nM. The test tubes were cooled to 4° C. before adding in AeSCP-2. Solution of purified recombinant AeSCP-2 was made in 10 mM K-phosphate buffer and 100 ul was added into the cholesterol containing test tubes at final concentration 8 pM per assay. The reaction was incubated at 4° C. overnight, and 250 ul of ice cold Lipidex-1000 (50% v/v) under continuously stirring was added into the test tubes. After 10' incubation on ice, Lipidex-1000-bound cholesterol was separated from SCP-2-bound cholesterol by centrifugation at 12,000×g at 4° C. for 3'. Two hundreds microlitter of supernatant (rAeSCP-2-bound cholesterol) were taken for radioactive measurement in a scintillation counter (Packard, Billerica, Mass.). Two controls were set up at the same time, one without AeSCP-2 and another without Lipidex- 1000, which were used to correct background. The data were plotted as Scatchard plot (Scatchard, 1949) with [bound/free] cholesterol as the Y-axis and molarity of bound cholesterol as the X-axis. The slope=−$K_a$ and $K_d$ was calculated as −1/$K_a$.

In vitro tissue culture—Staged 4th instars were dissected in insect saline (Riddiford et al., 1979) to obtain gut and carcass for in vitro tissue culture study. Dissected tissues were first washed in Grace's basal medium (Invitrogen), and cultured at 26° C. for 6 hours in 60 mm glass dishes in 2ml of Grace's basal medium containing 50 ug/ml penicillin, 50 ug/ml streptomycin and 100 ug/ml neomycin. Pure 20-hydroxyecdysone (Sigma) was dissolved in 95% ethanol, and the concentration was determined by UV spectrum absorption analysis at 243 nm wavelength (20E mg/ml=(OD 243× 480)/ϵ and the ϵ=12,670). Four microliters of 30 ng/ul of 20-hydroxyecdysone (20E) in 95% ethanol were added in the medium for hormone-treated tissue cultures to make the final concentration of 0.6 to 60 ng/ml 20E. Total RNA was extracted from cultured tissues and analyzed by Dot blotting. The experiment was repeated two times each with replicate samples. Soluble proteins were extracted from cultured tissues and analyzed by western blotting.

It is understood that the examples and embodiments described herein are for illustrative purposes only and that various modifications or changes in light thereof will be suggested to persons skilled in the art and are to be included within the spirit and purview of this application and scope of the appended claims. All publications, deposited sequences, patents, and patent applications cited herein are hereby incorporated by reference in their entirety for all purposes.

IV. References

Ausubel, F. M., Brent, R., Kingston, R. E., Moore, D. D., Seidman, J. G., Smith, J. A. and Struhl, K. 1993. Current Protocols in Molecular Biology. Current Protocols, Greene Publishing Associates, Inc. and John Wiley & Sons, Inc., New York.

Baum, C. L., Kansal, S. and Davidson, N. O. 1993. Regulation of sterol carrier protein-2 gene expression in rat liver and small intestine. J Lipid Res. 34(5):729–39.

Baum, C. L., Reschly, E. J., Gayen, A. K., Groh, M. E. and Schadick, K. 1997. Sterol carrier protein-2 overexpression enhances sterol cycling and inhibits cholesterol ester synthesis and high density lipoprotein cholesterol secretion. J. Biol. Chem. 272 (10) 6490–6498.

Beydon, P. and Lafont, R. 1987. Long-term cholesterol labeling as a convenient means for measuring ecdysteroid production and catabolism in vivo: application to the last larval instar of Pieris brassicae. Arch. Insect Biochem. Physiol. 5 (2): 139–154.

Bianchi, A. G. de and Capurro, M. de L. 1991. Musca domestica larval lipoprotein. Arch Insect Biochem Physiol. 17(1): 15–27.

Borovsky, D., Whisenton, L. R., Thomas, B. R. and Fuchs, M. S. 1986. Biosynthesis and distribution of ecdysone and 20-hydroxyecdysone in Aedes aegypti. Arch Insect Biochem Physiol. 3(1): 19–30.

Bun-ya, M., Muro, Y., Niki, T., Kondo, J. and Kamiryo, T. 2000. New aspects of sterol carrier protein 2 (nonspecific lipid-transfer protein) in fusion proteins and in peroxisomes. Cell Biochem Biophys. 32 Spring:107–16.

Christophers, S. R. 1960. *Aedes aegypti* (L.). The yellow fever mosquito. Its life history, bionomics and structure. Cambridge University Press, Cambridge.

Clayton, R. B. 1964. The utilization of sterols by insects. J Lipid Res. 5:3–19.

Colles, S. M., Woodford, J. K., Moncecchi, D., Myers-Payne, S. C., McLean, L. R., Billheimer, J.T. and Schroeder, F. 1995. Cholesterol interaction with recombinant human sterol carrier protein-2. Lipids. 30 (9): 795–803.

Dwivedy, A K. and Shukla, S P. 1982. Utilization of cholesterol by the adults of house fly, Musca domestica. Entomon. 7(4): 411–422.

Feldlaufer, M. F., Weirich, G. F., Imberski, R. B. and Svoboda, J. A. 1995. Ecdysteroid production in *Drosophila* melanogaster reared on defined diets. Insect Biochem Mol Biol. 25(6):709–12.

Frolov A, Cho T H, Billheimer J T, Schroeder F. 1996. Sterol carrier protein-2, a new fatty acyl coenzyme A-binding protein. J. Biol Chem. 271(50):31878–84.

FlyBase. 2001. flybase.bio.indiana.edu: 82

Fuchs, M., Hafer, A., Munch, C., Kannenberg, F., Teichmann, S., Scheibner, J., Stange, E. F. and Seedorf, U. 2001. Disruption of the sterol carrier protein 2 gene in mice impairs biliary lipid and hepatic cholesterol metabolism. J Biol Chem. 276(51):48058–65.

Gallegos, A. M., Schoer, J. K., Starodub, O., Kier, A. B., Billheimer, J. T. and Schroeder, F. 2000. A potential role for sterol carrier protein-2 in cholesterol transfer to mitochondria. Chem Phys Lipids. 105(1):9–29.

Gallegos, A. M., Atshaves, B. P., Storey, S. M., Starodub, O., Petrescu, A. D., Huang, H., McIntosh, A. L., Martin, G. G., Chao, H., Kier, A. B. and Schroeder, F. 2001. Gene structure, intracellular localization, and functional roles of sterol carrier protein-2. Prog Lipid Res. 40(6):498–563.

Gilbert, L. I. 1967. Lipid metabolism and function in insects. Adv. Insect Physiol. 4:169–211.

Gilbert L. I., Rybczynski, R. and Warren, J. T. 2002. Control and biochemical nature of the ecdysteroidogenic pathway. Annu Rev Entomol. 47:883–916.

Glatz, .J F. and Veerkamp, J. H. 1983. A radiochemical procedure for the assay of fatty acid binding by proteins. Anal Biochem. 132(1):89–95.

Grieneisen, M. L., Warren, J. T., Sakurai, S. and Gilbert, L. I. 1991. A putative route to ecdysteroids: metabolism of cholesterol in vitro by mildly disrupted prothoracic glands of Manduca sexta. Insect Biochem Mol. Biol. 21(1): 41–51.

Hagedom, H. H., O'Connor, J. D., Fuchs, M. S., Sage, B., Schlaeger, D. A. and Bohm, M. K. 1975. The ovary as a source of alpha-ecdysone in an adult mosquito. Proc Natl Acad Sci USA. 72(8):3255–9.

Jenkins, S. P., Brown, M. R. and Lea, A. O. 1992. Inactive prothoracic glands in larvae and pupae of Aedes aegypti: ecdysteroid release by tissues in the thorax and abdomen. Insect Biochem Molec Biol. 22(6):553–559.

Jouni, Z. E., Zamora, J. and Wells, M. A. 2002. Absorption and tissue distribution of cholesterol in Manduca sexta. Arch Insect Biochem Physiol. 49(3):167–75.

Kitamura, T., Kobayashi, S. and Okada, M. 1996. Regional expression of the transcript encoding sterol carrier protein x-related thiolase and its regulation by homeotic genes in the midgut of Drosophila embryos. Dev Growth Differ. 38 (4) 373–381.

Krebs, K. C., Brzoza, K. L. and Lan, Q. 2002. Use of Subtracted libraries and Macroarray to Isolate Developmentally Specific Genes from the Mosquito, Aedes aegypti. Insect Biochem. Mol. Biol. In press.

Kuthiala, A. and Ritter, K. S. 1988a. Uptake of cholesterol and cholastanol by the intestine, hemolymph, and fat body of Heliothis zea. Arch Insect Biochem Physiol. 7 (4) p. 225–236.

Kuthiala, A. and Ritter, K. S. 1988b. Esterification of cholesterol and cholastanol in the whole body, tissues, and frass of Heliothis zea. Arch Insect Biochem Physiol. 7(4): 237–248.

Lasser, N. L. and Clayton, R. B. 1966. The intracellular distribution of sterols in Eurycotis floridana and its possible relation to subcellular membrane structures. J. Lipid Res. 7:413–421.

Mannaerts, G. P., Van Veldhoven, P. P. and Casteels, M. 2000. Peroxisomal lipid degradation via beta- and alpha-oxidation in mammals. Cell Biochem Biophys. 32 Spring: 73–87.

McLean, M. P., Puryear, T. K., Khan, I., Azhar, S., Billheimer, J. T., Orly, J. and Gibori, G. 1989. Estradiol regulation of sterol carrier protein 2 independent of cytochrome P450 side-chain cleavage expression in the rat corpus luteum. Endocrinology. 125(3): 1337–1344.

Myers-Payne, S. C., Fontaine, R. N., Loeffler, A., Pu, L., Rao, A. M., Kier, A. B., Wood, W. G. and Schroeder, F. 1996. Effects of chronic ethanol consumption on sterol transfer proteins in mouse brain. J Neurochem. 66(1): 313–20.

NCBI, 2002. www.ncbi.nlm.nih.gov/Structure/lexington/lexington.cgi

Nes, W. D., Lopez, M., Zhou, W., Guo, D. A., Dowd, P. F. and Norton, R. A. 1997. Sterol utilization and metabolism by Heliothis zea. Lipids. 32 (12): 1317–1323.

Noda, H., Wada, K. and Saito, T. 1979. Sterols in Laodelphax striatellus with special reference to the intracellular yeast-like symbiotes as a sterol source. J Insect Physiol. 25 (5): 443–447.

Ohba, T., Holt, J. A., Billheimer, J. T. and Strauss, J. F. 3rd. 1995. Human sterol carrier protein x/sterol carrier protein 2 gene has two promoters. Biochemistry. 34(33): 10660–8.

Ossendorp, B. C., van Heusden, G. P. and Wirtz, K. W. 1990. The amino acid sequence of rat liver non-specific lipid transfer protein (sterol carrier protein 2) is present in a high molecular weight protein: evidence from cDNA analysis. Biochem Biophys Res Commun. 168(2):631–6.

Pfeifer, S. M., Sakuragi, N., Ryan, A., Johnson, A. L., Deeley, R. G., Billheimer, J. T., Baker, M. E. and Strauss, J. F 3rd. 1993a. Chicken sterol carrier protein 2/sterol carrier protein x: cDNA cloning reveals evolutionary conservation of structure and regulated expression. Arch Biochem Biophys. 304(1):287–93.

Pfeifer, S. M., Furth, E. E., Ohba, T., Chang, Y. J., Rennert, H., Sakuragi, N., Billheimer, J. T. and Strauss, J. F III. 1993b. Sterol carrier protein 2: A role in steroid hormone synthesis? J. Steroid Biochem. Mol. Biol. 47 (1–6) 167–172.

Puglielli, L., Rigotti, A., Greco, A. V., Santos, M. J. and Nervi, F. 1995. Sterol carrier protein-2 is involved in cholesterol transfer from the endoplasmic reticulum to the membrane in human fibroblasts. J Biol Chem. 270(32): 18723–6.

Rennert, H., Amsterdam, A., Billheimer, J. T. and Strauss J F 3rd. 1991. Regulated expression of sterol carrier protein 2 in the ovary: a key role for cyclic AMP. Biochemistry. 130(47):11280–5.

Riddiford, L. M.; Curtis, A. T. and Kiguchi, K. 1979. Culture of the epidermis of the tobacco hornworm Manduca sexta [Control by hormones in vitro]. Tissue-Cult-Assoc-Man. 5 (1) p. 975–985.

Ritter, K S. 1984. Metabolism of DELTA-0-sterols, DELTA-5-sterols and DELTA-7-sterols by larvae of Heliothis zea. Arch Insect Biochem Physiol. 1(3): 281–296.

Ritter, K S. 1986. Utilization of DELTA-5,7- and DELTA-8-sterols by larvae of Heliothis zea. Arch Insect Biochem Physiol. 3(4): 349–362.

Ritter, K. S. and Nes, W. R. 1981. The effects of cholesterol on the development of Heliothis zea. J. Insect Physiol. 27(3): 175–182.

Scatchard, G. 1949. The attractions of proteins for small molecules and ions. Ann New York Acad Sci. 51:660–672.

Schoer, J. K., Gallegos, A. M., McIntosh, A. L., Starodub, O., Kier, A. B., Billheimer, J. T. and Schroeder, F. 2000. Lysosomal membrane cholesterol dynamics. Biochem. 39(26):7662–77.

Schroeder, F., Frolov, A., Starodub, O.; Atshaves, B. B., Russell, W., Petrescu, A., Huang, H., Gallegos, A. M., McIntosh, A., Tahotna, D., Russell, D. H., Billheimer, J. T., Baum, C. L. and Kier, A. B. 2000. Pro-sterol carrier protein-2: role of the N-terminal presequence in structure, function, and peroxisomal targeting. J Biol Chem. 275 (33):25547–55.

Schroeder, F., Gallegos, A. M., Atshaves, B. P., Storey, S. M., McIntosh, A. L., Petrescu, A. D., Huang, H., Starodub, O., Chao, H., Yang, H., Frolov, A. and Kier, A. B. 2001. Recent advances in membrane microdomains: rafts, caveolae, and intracellular cholesterol trafficking. Exp Biol Med (Maywood). 226(10):873–90.

Sedensky, M. M., Siefker, J. M. and Morgan, P. G. 2001. Model organisms: new insights into ion channel and transporter function. Stomatin homologues interact in *Caenorhabditis elegans*. Am J Physiol Cell Physiol. 280 (5):C1340–8.

Seedorf, U. and Assmann, G. 1991. Cloning, expression, and nucleotide sequence of rat liver sterol carrier protein 2 cDNAs. J Biol Chem. 266(1):630–6.

Seedorf, U., Engel, T., Assmann, G., Leenders, F. and Adamski, J. 1995. Intrinsic sterol-and phosphatidylcholine transfer activities of 17 beta-hydroxysteroid dehydrogenase type IV. J Steroid Biochem Mol Biol. 55(5–6): 549–53.

Seedorf U, Raabe M, Ellinghaus P, Kannenberg F, Fobker M, Engel T, Denis S, Wouters F, K W, Wanders R J, Maeda N, Assmann G. 1998. Defective peroxisomal catabolism of branched fatty acyl coenzyme A in mice lacking the sterol carrier protein-2/sterol carrier protein-x gene function. Genes Dev. 12(8):1189–201.

Seedorf, U., Ellinghaus, P. and Roch Nofer J. 2000. Sterol carrier protein-2. Biochim Biophys Acta. 1486(1):45–54.

Spates, G. E.; DeLoach, J. R. and Chen, A. C. 1988. Ingestion, utilization and excretion of blood meal sterols by the stable fly, Stomoxys calcitrans. J Insect Physiol. 34 (11): 1055–1061.

Stolowich, N. J., Petrescu, A. D., Huang, H., Martin, G. G., Scott. A. I. and Schroeder, F. 2002. Sterol carrier protein-2: structure reveals function. Cell. Mol. Life Sci. 59(2): 193–212.

Soulages, J. L. and Brenner, R. R. 1991. Study on the composition-structure relationship of lipophorins. J Lipid Res. 32(3): 407–415.

Steinschneider, A., McLean, M. P., Billheimer, J. T., Azhar, S. and Gibori, G. 1989. Protein kinase C catalyzed phosphorylation of sterol carrier protein 2. Endocrinology. 125(1):569–71.

Sviridov, D. 1999. Intracellular cholesterol trafficking. Histol Histopathol. 14(1): 305–19.

Svoboda, J. A and Weirich, G. F. 1995. Sterol metabolism in the tobacco hornworm, Manduca sexta-A review. Lipids. 30 (3): 263–267.

Tan, H., Okazaki, K., Kubota, I., Kamiryo, T. and Utiyama, H. 1990.A novel peroxisomal nonspecific lipid-transfer protein from *Candida tropicalis*. Gene structure, purification and possible role in beta-oxidation. Eur J Biochem. 190(1):107–12.

van Heusden, G. P., Bos, K. and Wirtz, K. W. 1990. The occurrence of soluble and membrane-bound non-specific lipid transfer protein (sterol carrier protein 2) in rat tissues. Biochim Biophys Acta. 1046(3):315–21.

van Noort, M., Rommerts., F. F. G., van Amerongen, A. and Wirtz, K. W. A. 1988. Intracellular redistribution of SCP-2 in Leydig cells after hormonal stimulation may contribute to increased pregnenolone production. Biochem. Biophysic. Res. Commun. 154(1): 60–65

Xu, T., Bowman, E. P., Glass, D. B. and Lambeth, J. D. 1991. Stimulation of adrenal mitochondrial cholesterol side-chain cleavage by GTP, steroidogenesis polypeptide (SAP), and sterol carrier protein-2: GTP and SAP act synergistically. J.Biol. Chem. 266(11): 6801–6807

---

What is claimed is:

1. A method of identifying whether a compound is an agonist or antagonist of *Aedes aegypti* sterol carrier protein-2 (AeSCP-2) cholesterol binding activity, comprising the steps of:
  (a) incubating an AeSCP-2 polypeptide comprising the amino acid sequence set forth in SEQ ID NO:3 with cholesterol in the presence of a compound; and
  (b) measuring the ability of the compound to enhance or block the interaction between the AeSCP-2 polypeptide and cholesterol to thereby identify an agonist or antagonist effective in altering AeSCP-2 cholesterol binding activity.

2. A method for identifying a compound which bind to an *Aedes aegypti* sterol carrier protein-2 (AeSCP-2) polypeptide having the amino acid sequence set forth in SEQ ID NO:3, comprising the steps of:
  (a) contacting an AeSCP-2 polypeptide having the amino acid sequence set forth in SEQ ID NO:3 with the compound to be screened, under conditions to permit binding of the compound to the AeSCP-2 polypeptide, said binding being associated with a detectable signal in response to the binding of the AeSCP-2 polypeptide with the compound; and
  (b) determining whether the compound binds to the AeSCP-2 polypeptide by detecting the presence or absence of the signal generated from the binding of the compound with the AeSCP-2 polypeptide.

* * * * *

SEQUENCE LISTING

```
<160> NUMBER OF SEQ ID NOS: 3

<210> SEQ ID NO 1
<211> LENGTH: 333
<212> TYPE: DNA
<213> ORGANISM: Aedes aegypti

<400> SEQUENCE: 1
atgtctctga agtccgacga agtttttcgcc aagatcgcta agcgtctgga gagcatcgac         60
cccgccaacc gtcaggtcga gcacgtgtac aagttcagaa tcacccaggg tggcaaggtt        120
gtcaagaact gggttatgga tctgaagaac gtcaagctgg tcgagtccga cgatgccgcc        180
gaggccaccc tgaccatgga ggatgacatc atgttcgcca tcggaaccgg tgccctgccc        240
gccaaggaag ccatggccca ggacaagatg gaagtcgatg gacaagttga gctgatcttc        300
ctgctggagc cattcattgc ctcgctgaag taa                                     333
```

```
<210> SEQ ID NO 2
<211> LENGTH: 571
<212> TYPE: DNA
<213> ORGANISM: Aedes aegypti

<400> SEQUENCE: 2
gatcagtttc gagttgtcca cttgaagttc tgttgaaaaa ccaaaccacc ctccaaaatg      60
tctctgaagt ccgacgaagt tttcgccaag atcgctaagc gtctggagag catcgacccc     120
gccaaccgtc aggtcgagca cgtgtacaag ttcagaatca cccagggtgg caaggttgtc     180
aagaactggg ttatggatct gaagaacgtc aagctggtcg agtccgacga tgccgccgag     240
gccaccctga ccatggagga tgacatcatg ttcgccatcg gaaccggtgc cctgcccgcc     300
aaggaagcca tggcccagga caagatgaa gtcgatggac aagttgagct gatcttcctg      360
ctggagccat tcattgcctc gctgaagtaa aatgcgtgac gcggcccttg tgaataccaa     420
tcattgcatg tgcttgcctc gtttaatcag agcgaatgtc atgtcatcca aactactgtg     480
ttgtaactta ttattttcct gtatcgcgat ttcggcatca ttaaaacgta ttttgtaaag     540
taaaaaaaaa aaaaaaaaa aaaaaaaaaa a                                      571

<210> SEQ ID NO 3
<211> LENGTH: 110
<212> TYPE: PRT
<213> ORGANISM: Aedes aegypti

<400> SEQUENCE: 3

Met Ser Leu Lys Ser Asp Glu Val Phe Ala Lys Ile Ala Lys Arg Leu
1               5                   10                  15

Glu Ser Ile Asp Pro Ala Asn Arg Gln Val Glu His Val Tyr Lys Phe
            20                  25                  30

Arg Ile Thr Gln Gly Gly Lys Val Val Lys Asn Trp Val Met Asp Leu
        35                  40                  45

Lys Asn Val Lys Leu Val Glu Ser Asp Asp Ala Ala Glu Ala Thr Leu
    50                  55                  60

Thr Met Glu Asp Asp Ile Met Phe Ala Ile Gly Thr Gly Ala Leu Pro
65                  70                  75                  80

Ala Lys Glu Ala Met Ala Gln Asp Lys Met Glu Val Asp Gly Gln Val
                85                  90                  95

Glu Leu Ile Phe Leu Leu Glu Pro Phe Ile Ala Ser Leu Lys
            100                 105                 110
```